United States Patent
Popp et al.

(10) Patent No.: US 10,170,210 B2
(45) Date of Patent: Jan. 1, 2019

(54) DEVICE SYSTEM FOR MILITARY AND/OR HUMANITARIAN OPERATIONS, IN PARTICULAR A MOBILE DECONTAMINATION SYSTEM

(71) Applicant: Kaercher Futuretech GmbH, Schwaikheim (DE)

(72) Inventors: Thomas Popp, Stuttgart (DE); Ulli Reinhardt, Backnang (DE); Daniel Ruprecht, Fellbach (DE)

(73) Assignee: KAERCHER FUTURETECH GMBH, Schwaikheim (DE)

( * ) Notice: Subject to any disclaimer, the term of this patent is extended or adjusted under 35 U.S.C. 154(b) by 19 days.

(21) Appl. No.: 15/171,096

(22) Filed: Jun. 2, 2016

(65) Prior Publication Data
US 2016/0276048 A1    Sep. 22, 2016

Related U.S. Application Data

(63) Continuation of application No. PCT/EP2013/075581, filed on Dec. 4, 2013.

(51) Int. Cl.
*G21F 9/00* (2006.01)
*E04H 1/12* (2006.01)
(Continued)

(52) U.S. Cl.
CPC ............... *G21F 9/002* (2013.01); *A61L 2/18* (2013.01); *B08B 3/08* (2013.01); *B08B 3/10* (2013.01); *E04H 1/1277* (2013.01); *B60P 3/005* (2013.01)

(58) Field of Classification Search
CPC ... G21F 9/002; B08B 3/10; B08B 3/08; A61L 2/18; E04H 1/1277
See application file for complete search history.

(56) References Cited

U.S. PATENT DOCUMENTS 5,301,701 A  *  4/1994  Nafziger ................... B08B 3/10
                                                       134/108
6,058,718 A  *  5/2000  Forsberg ................. C02F 1/008
                                                        62/125
(Continued)

FOREIGN PATENT DOCUMENTS

BE          701367           12/1967
DE      19653731 A1           8/1998
(Continued)

OTHER PUBLICATIONS

International Preliminary Report on Patentability for International Application No. PCT/EP2013/075581, dated Jun. 16, 2016.
(Continued)

*Primary Examiner* — Regina M Yoo
(74) *Attorney, Agent, or Firm* — Jason H. Vick; Sheridan Ross, PC

(57)  ABSTRACT

A device system for military and/or humanitarian operations, in particular a mobile decontamination system, comprises a plurality of power-operated units, accessory parts and operating supplies, which together determine a functional scope of the device system. The power-operated units, accessory parts and operating supplies are mounted on a base plate by means of a retaining structure, said base plate having a defined placement surface and anchoring elements. The anchoring elements enable detachable anchoring of the base plate together with the retaining structure to a transport means, in particular to a transport vehicle. The retaining structure is formed from a plurality of self-supporting, structurally identical, cuboid-shaped frames, which are arranged next to each other and/or on top of each other and are fastened to the base plate. The frames each have eight corner pieces and twelve edge profile elements, which together enclose a defined storage volume. The power-operated units, accessory parts and operating supplies are
(Continued)

arranged in the defined storage volumes and, preferably, at least the majority of the power-operated units and operating supplies are retained in the frames even during operation of the device system.

14 Claims, 6 Drawing Sheets

(51) Int. Cl.
*A61L 2/18* (2006.01)
*B08B 3/08* (2006.01)
*B08B 3/10* (2006.01)
*B60P 3/00* (2006.01)

(56) References Cited

U.S. PATENT DOCUMENTS

| | | | | |
|---|---|---|---|---|
| 6,182,453 | B1* | 2/2001 | Forsberg | B01D 5/0072 62/125 |
| 2010/0031977 | A1* | 2/2010 | Sales | B08B 3/02 134/39 |
| 2010/0299826 | A1 | 12/2010 | Grcevic | |
| 2016/0160752 | A1* | 6/2016 | Kuhlmann | F02B 63/048 290/1 A |

FOREIGN PATENT DOCUMENTS

| | | | |
|---|---|---|---|
| DE | 10345351 A1 | 5/2005 | |
| EP | 2617630 A2 | 7/2013 | |
| WO | WO 03/046314 | 6/2003 | |
| WO | WO-03080475 A1 * | 10/2003 | .......... B65D 88/121 |
| WO | WO 2006/000795 | 1/2006 | |

OTHER PUBLICATIONS

International Standard—ISO 668; Sixth Edition Aug. 1, 2013.
Futuretech Kärcher Group "Decocontain 3000 GDS: Containerised Full Decontamination System" Aug. 2011.
International Search Report for International Application No. PCT/EP2013/075581, dated Jul. 30, 2014.
Written Opinion for International Application No. PCT/EP2013/075581, dated Jul. 30, 2014.

* cited by examiner

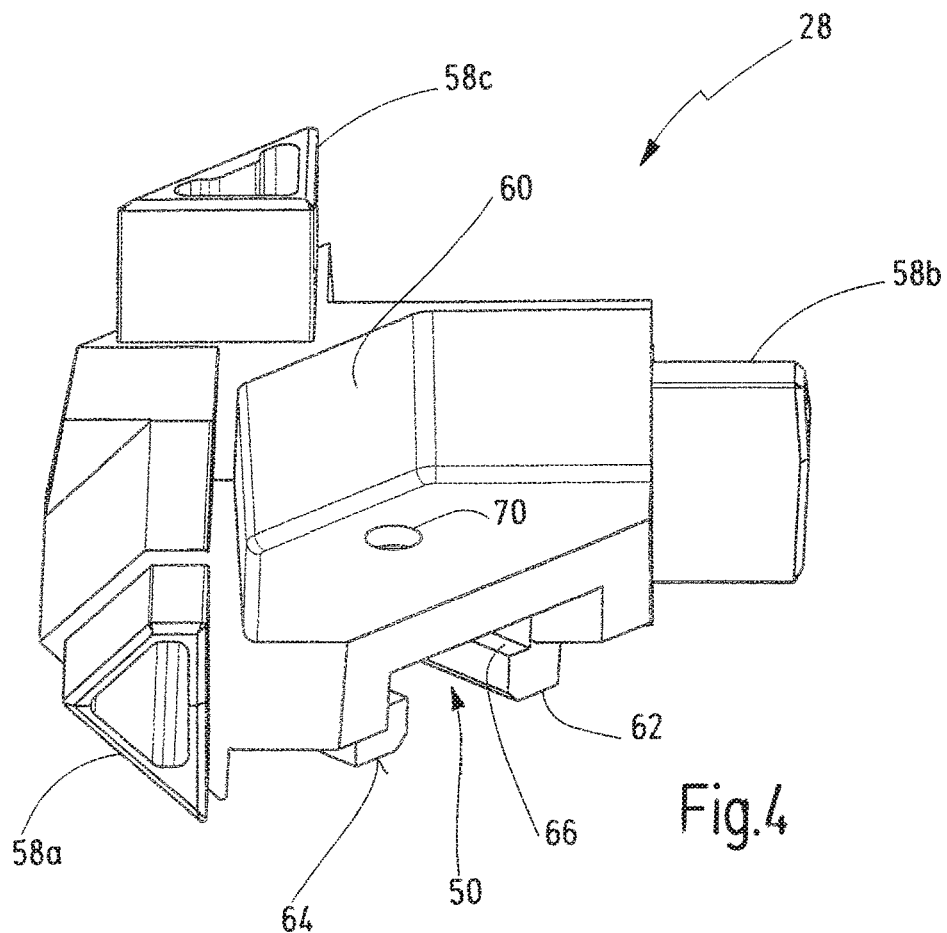
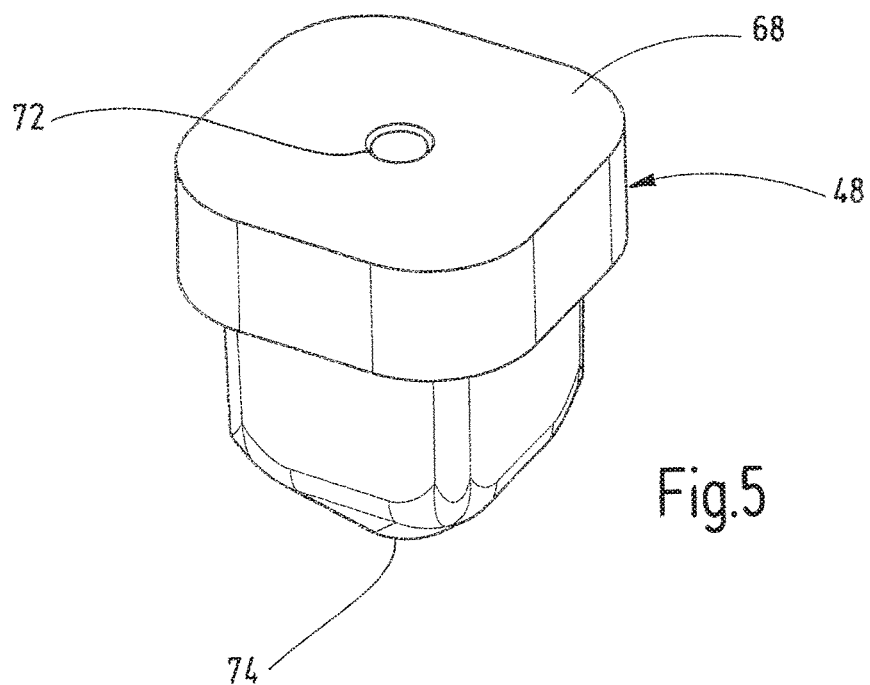

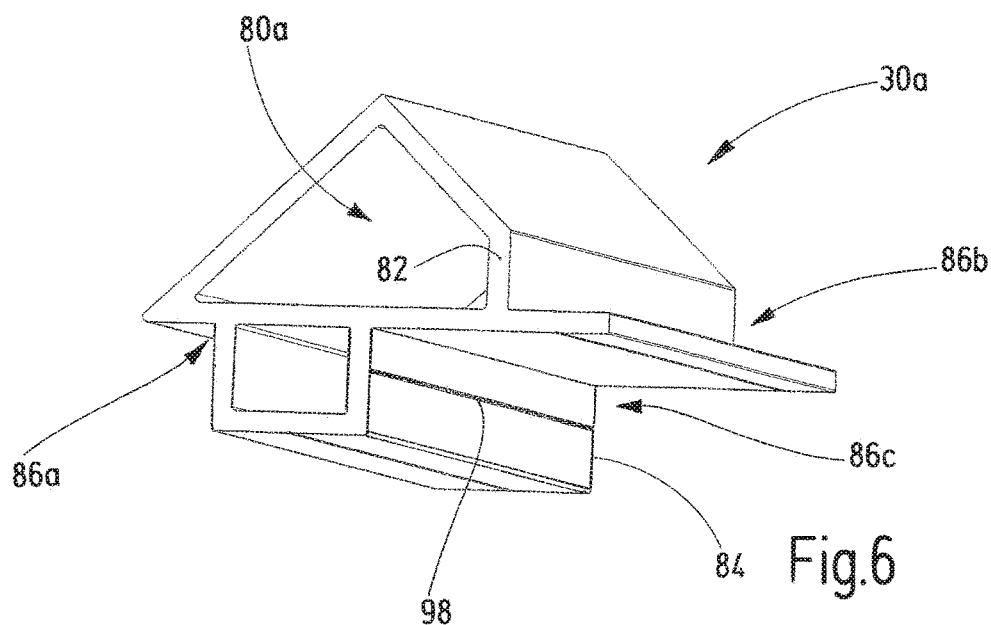
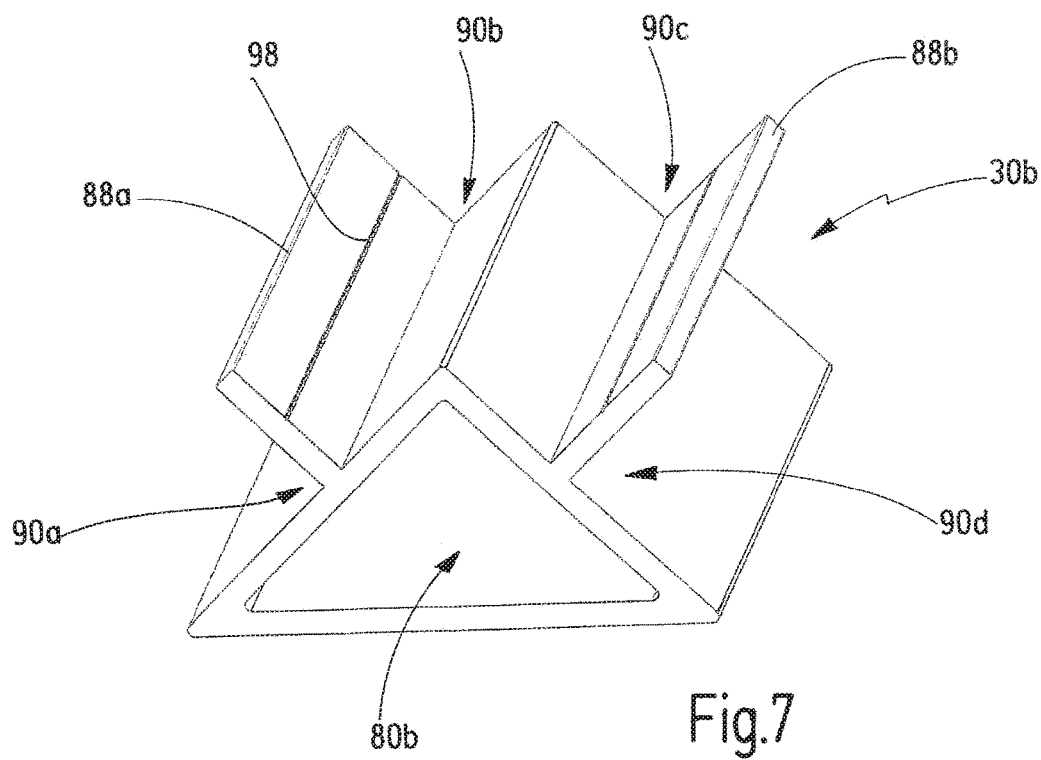

DEVICE SYSTEM FOR MILITARY AND/OR HUMANITARIAN OPERATIONS, IN PARTICULAR A MOBILE DECONTAMINATION SYSTEM

CROSS REFERENCES TO RELATED APPLICATIONS

This application is a continuation of international patent application PCT/EP2013/075581, filed on Dec. 4, 2013 and designating the U.S. The entire content of this prior application is incorporated herein by reference.

BACKGROUND OF THE INVENTION

The present invention relates to a device system for military and/or humanitarian operations, and in particular to a mobile decontamination system designed for at least one of radioactive decontamination, disinfection and detoxification.

A prior art device system is, for example, a decontamination system called DECOCONTAIN 3000 GDS available from the company Kärcher Futuretech GmbH, which has its headquarters in 71409 Schwaikheim, Germany.

This prior art decontamination system is a typical example of a device system for military or humanitarian operations. It contains a plurality of power-operated units, such as one or more pumps, an aerosol generator, heaters and control devices, and also a plurality of accessory parts, such as spray lances or tubes, and a plurality of operating supplies, such as decontaminants in particular. The units, accessory parts and operating supplies determine and delimit the functional scope, which is typically defined by the buyers and users of a system of this type within the scope of a tender and/or on the basis of a list of requirements. The overall arrangement of the units, accessory parts and operating supplies is generally so heavy in the case of such systems that the systems can only be brought to their place of use by suitable transport means, such as a heavy goods vehicle or a helicopter. Such device systems are very often constructed in containers which conform to ISO standard 668 for sea freight containers. The containers are then anchored to the transport vehicles. The device systems are often used from the container and from the transport vehicle, but in principle could also be used remote from the transport vehicle.

One challenge for the manufacturers of such device systems therefore lies in housing a functional scope requested by the user within a spatial volume likewise specified by the user. By way of example, the spatial volume may be dependent on the maximum dimensions and weights that can be transported by a particular transport vehicle. The device systems are generally matched to the specific user requirements, which results in a high development and production outlay with comparatively small quantities. In particular, the optimal spatial planning for a new device system continues to pose a number of great challenges to the manufacturer.

The above-mentioned decontamination system DECOCONTAIN 3000 GDS is constructed in a 20 foot ISO container. A plurality of supporting columns is fastened within the container and forms a retaining structure for the heavy units. The position of the individual supporting columns within the container is determined by the spatial arrangement of the units, accessory parts and operating supplies within the container and by structural conditions. If a user wishes to modify the functional scope, for example because said user wishes to decontaminate a greater number of temperature-sensitive small parts per hour, this often requires a fundamental re-build of the system.

DE 103 45 351 A1 describes another mobile decontamination system in which function-determining units, accessory parts and operating supplies are housed in transportable containers. The details of the retaining structure in the containers are only partially visible in the drawings. In principle, however, this case too relates to a device system in which the spatial arrangement of the individual components in the containers has been individually developed in accordance with a predefined functional scope.

Further mobile decontamination systems are disclosed by U.S. Pat. No. 2010/0299826 A1 and WO 03/046314 A1. These systems as well have a container in which the function-determining components are individually housed.

SUMMARY OF THE INVENTION

In view of this background, it is an object of the present invention to provide a device system of the type described above which efficiently enables an adaptation to individual user requirements. A further object of the invention is to provide a device system of the type described above which the manufacturer can easily and efficiently adapt to individual user requirements. A further object of the invention is to provide a device system of the type described above which can be produced economically with individual functional scopes.

In accordance with one aspect of the invention, there is provided a mobile decontamination system for at least one of radioactive decontamination, disinfection and detoxification, the system comprising a plurality of power-operated units including at least one electrical pump for recirculating, conveying or discharging liquids, a heater and a process controller for controlling the at least one pump and the heater, a water tank, a plurality of accessory parts, and operating supplies including cleaning agents or decontaminants, said power-operated units, accessory parts and operating supplies together defining a functional scope for the at least one of radioactive decontamination, disinfection and detoxification, a load-bearing base plate having a defined placement surface and anchoring elements, which enable detachable anchoring of the base plate to a transport vehicle, and a retaining structure fastened on the placement surface and designed to hold the power-operated units, the water tank, the accessory parts and the operating supplies on the base plate during transport, wherein the retaining structure is formed from a plurality of self-supporting, structurally identical, cuboid-shaped frames which are arranged next to each other or on top of each other and which are fastened to the base plate, wherein the frames each have eight corner pieces and twelve edge profile elements which together enclose a defined storage volume per frame, wherein at least a majority of the power-operated units and the water tank are stationary installed in respective ones of the defined storage volumes so as to be operated for the at least one of radioactive decontamination, disinfection and detoxification while they are accommodated in the defined storage volumes.

In accordance with another aspect of the invention, there is provided a device system for military or humanitarian operations, comprising a plurality of power-operated units, accessory parts and operating supplies which together determine a functional scope of the device system, and comprising a load-bearing base plate having a defined placement surface and anchoring elements, which enable detachable anchoring to a transport means, and comprising a retaining structure which is fastened on the placement surface and which is designed to hold the units on the base plate, wherein the retaining structure is formed from a plurality of self-supporting, structurally identical, cuboid-shaped frames, which are arranged next to one another or on top of each other and are fastened to the base plate, wherein the frames each have eight corner pieces and twelve edge profile elements which together enclose a defined storage volume, and wherein the power-operated units, accessory parts and operating supplies are consistently arranged in the defined storage volumes On account of the frames, the new system has a modular and therefore rather flexible construction. Each frame forms a defined storage volume, in which one or more units, accessory parts and/or operating supplies can be housed during transport and during operation, as the case may be. In some preferred exemplary embodiments the units, accessory parts and operating supplies of the new system are arranged exclusively in the defined storage volumes of the frames. By contrast, however, it is conceivable in other exemplary embodiments for individual units, accessory parts and operating supplies of the device system to be arranged outside a frame, for example because a unit is very large or because some accessory parts are very bulky. In these cases, however, at least some further units and accessory parts and operating supplies are arranged in the defined storage volumes of the frames. The new device system thus has a plurality of frames, which accommodate the function-determining units, accessory parts and operating supplies at least predominantly and preferably exclusively. This holds true, preferably, both for transport and for operation of the system at the place of use.

The self-supporting frames are stable enough to accommodate and support the integrated units, accessory parts and/or operating supplies in the manner of a small container. Accordingly, it is generally possible in the case of the new system to take down the frames comprising the units, accessory parts and/or operating supplies from the load-bearing base plate, either individually or in their entirety. In some exemplary embodiments the frames have retaining eyelets for fastening a crane rope and/or defined openings, with which the fork of a forklift truck can engage. The retaining eyelets and/or openings facilitate the assembly of the new device system for the manufacturer and also facilitate the replacement, maintenance and repair of faulty components.

In addition the self-supporting, structurally identical frames form some sort of a building block system having cuboid-shaped "blocks", which can be very easily combined within a container or even on an open load-bearing base plate to form an overall system. The housing of the units, accessory parts and operating supplies in the frames therefore makes it easier for the manufacturer to assemble a new device system in accordance to individual user requirements. Furthermore, the previously necessary effort to adapt a retaining structure for the units, accessory parts and operating supplies to the individual user requirements and to produce these units as necessary on the basis of a list of special requirements is eliminated. Since the frames are structurally identical to one another and preferably have identical corner pieces, the production costs for the retaining structure are more favorable compared with the previous device systems, even if "unnecessary" corners and edge profile elements are incorporated in the new device system.

In summary, the new system therefore facilitates the planning, construction and production of a device system for military and/or humanitarian operations that is adapted to individual requirements. Therefore, the above-mentioned objects are completely achieved.

In a preferred refinement, the frames occupy a central region of the placement surface, such that a free edge region remains on the base plate on at least two sides, preferably on at least three sides.

In this refinement the retaining structure with the frames is, to a certain extent, the center of the device system on the base plate. Alternatively, it is conceivable in other embodiments to arrange the frames in the edge region of the base plate such that the central region of the placement surface remains free. The preferred embodiment has the advantage that the edge region can be enlarged relatively easily by using panels, flaps, or the like when the device system is to be put into operation at the place of use. The preferred refinement therefore facilitates the use of the new device system and enables a very efficient use of the storage volume of commercial 20 foot or 40 foot containers according to ISO 668.

In a further refinement the system has at least one mobile working platform, which can be positioned at the height of the base plate at the edge region.

In preferred exemplary embodiments the mobile working platform can be fastened to the edge region of the base plate, for example latched in suitably formed receptacles on the base plate. In other exemplary embodiments the mobile working platform is the side wall of a container, which is pivotably mounted on the base plate and can be folded down in such a way that it can be brought into line with the base plate largely parallel to the base plate. This refinement makes it possible during operation to provide, in a very simple manner, an enlarged edge region around the frames centrally arranged on the base plate. This refinement is therefore particularly suitable in cases in which the base plate together with the frames is fastened on a transport vehicle, such as a heavy goods vehicle. The working platform can be removed or pivoted for transport.

In a further refinement the power-operated units are mounted in the frames in a stationary manner.

In this refinement, the units are always operated within the frames. In preferred exemplary embodiments the units include at least one of the following components: a generator for generating electrical power, one or more pumps for recirculating, conveying and/or discharging liquids, one or more pumps for generating negative pressure, a burner and/or an electrical heater for heating liquids to be discharged, decontaminants and/or other chemicals, filters, process control devices and a control panel. The stationary fastening of these units in the frames simplifies the assembly of the units in the new device systems and promotes interruption-free operation during use.

In a further refinement the frames have a uniform modular dimension in terms of width, depth and/or height.

In this refinement the frames are not only structurally identical, but in at least one dimension and preferably in at least two dimensions have an integer multiple of a defined basic measurement. In preferred exemplary embodiments the device system has a retaining structure having a plurality of frames which have identical measurements in respect of width, height and depth. These refinements enable a very economical and flexible planning, construction and production of device systems of which the functional scope is individually adapted to user requirements.

In a further refinement the plurality of frames includes first frames and second frames, wherein the first frames have a first footprint having a first width and a first depth and a first height, wherein the second frames have a second footprint having a second width and a second depth and a second height, wherein the second depth is the same as the first depth, and wherein the second height is approximately a third of the first height. The second width is advantageously twice the first width. In some exemplary embodiments, however, the first width and second width are the same. Preferably, the entire retaining structure of the device system consists of the first and second frames.

In this refinement the first frames may have half the width of the second frames. On the other hand, the first frames are much taller than the second frames. The retaining structure is thus formed on the one hand of narrow, tall frames and on the other hand of flat and preferably wide frames. All frames advantageously have the same depth. Two narrow first frames exactly match, with half the width, a flat second frame part. The wide flat frames are very suitable for receiving liquid tanks, since a tank of this type is very heavy when full and therefore prefers a low center of gravity of the device system. The narrow, tall frames are advantageously used to receive the units that can be more easily installed and operated in the higher frames. Stacked on top of each other, a device system that can be configured in a very flexible manner having a very small number of different parts for the retaining structure can be produced.

In a further refinement the first width is approximately 90 cm and the first depth is approximately 200 cm. The first height is approximately 150 cm. Here, the term "approximately" denotes a tolerance range of +/−15%.

These dimensions for the first and second frames have proven to be optimal dimensions under many considerations and following many tests performed by the applicant in order to construct and produce device systems for military operations and in particular decontamination systems for radioactive decontamination, disinfection and/or detoxification of items of military equipment. It is particularly advantageous when the clear inner dimension of the frames in width is at least 80 cm. These dimensions make it possible to house many different units. Here, the dimensions limit the maximum weight of an individual module on account of the encompassed storage volume. They also make it possible to produce a retaining structure that can be used in a flexible manner and that is suitable for transport with numerous military transport vehicles and aircraft.

In a further refinement the system has at least one liquid tank, which is permanently fastened in one of the frames. The frame is advantageously a flat second frame below one or two tall narrow frames, wherein the latter are arranged and fastened on the flat second frame.

This refinement makes advantageous use of the possibilities already discussed further above and has proven its worth in particular for producing a decontamination system, since it enables easy access to the units at an ergonomic working height and enables a relatively low center of gravity in a ready-to-use system.

In a further refinement the corner pieces each have three pins arranged orthogonally to one another, wherein each pin is permanently connected to an edge profile element.

In preferred exemplary embodiments the pins of the corner pieces are glued, welded and/or screwed to the connected edge profile elements. In the preferred exemplary embodiments the edge profile elements are cast profile elements each having at least one hollow chamber, into which the pins of the corner pieces protrude. The cast profile elements are preferably produced by means of a gravity casting process and in particular a permanent mold casting process, because this is the most advantageous production process for the intended use of the corner pieces. The embodiments enable a largely smooth outer contour of the frames, which is advantageous in terms of cleaning and utilization of space. Furthermore, it is preferred in some exemplary embodiments when the pins and hollow chambers have a polygonal cross section, since this counteracts a rotation of the edge profile elements relative to the pins. In preferred exemplary embodiments the corner pieces are diecast parts made of aluminum. Furthermore, it is preferred when all corner pieces of the frames are identical, in order to reduce the number of different parts and production costs.

It has been found that with corner pieces of this type very stable frames can be produced, which on account of their stability can receive very heavy units on a sustained basis. The preferred formation of the pins and edge profile elements and the permanent connection thereof facilitate an operation of the units, even under the harsh conditions of use posed by a military operation.

In a further refinement the corner pieces each have a pocket-like indentation, which is delimited on one side by a U-shaped profile element, which forms an undercut in the indentation.

This refinement has proven to be an optimal variant in order to enable a flexible and at the same time robust connection of two frames to one another. The undercut in the pocket-like indentation enables the insertion of lock pins, with which two corner pieces can be coupled in a very simple and robust manner. The pocket-like indentation here enables high material strengths for the lock pin head, which is advantageous in view of the high forces that must be taken up by the frames and in particular the corner pieces thereof.

In a further refinement the U-shaped profile element has a planar outer face, which forms a defined elevation on the associated corner piece.

In this refinement the planar outer face forms a defined footprint area, which enables a very stable and positionally accurate connection between two corner pieces contacting one another. In preferred exemplary embodiments the frames each rest only on the defined footprint areas of four corner pieces. Here, the U-shaped profile elements form the highest or lowest projection in the outer contour of the frames, such that the weight of the frames inclusive of the units, accessory parts and operating supplies arranged therein rests on the corner pieces. This refinement avoids transverse loads at individual points on the edge profile elements and has proven to be a very favorable implementation in particular for receiving heavy units or liquid tanks.

In a further refinement the system has a plurality of T-shaped lock pins, with which adjacently arranged corner pieces of two frames arranged on top of each other are mechanically connected.

In this refinement the frames arranged on top of each other are advantageously fixed in the horizontal direction by T-shaped lock pins. Here, the refinement makes use of the force of gravity. The device system in the preferred exemplary embodiments additionally has a detachable clamping mechanism, with the aid of which the frames arranged on top of each other can be clamped to one another in the vertical direction. In some exemplary embodiments the clamping mechanism has an eccentric in order to apply a high clamping force. In other exemplary embodiments the clamping mechanism has a turnbuckle having two oppositely directed screw threads arranged axially relative to one another. The use of the T-shaped lock pins in conjunction with the U-shaped profile elements of the above refinement has proven to be a very economical and at the same time very robust implementation for the coupling of the frames. Furthermore, the corner pieces and lock pins can also be used advantageously to fasten each lowermost frame to the base plate, whereby the number of different parts used is reduced further still.

In a further refinement the corner pieces are produced from a first material and the lock pins are produced from a second material, which is softer than the first material.

This refinement has the advantage that the lock pins act as wearing parts to a certain extent. The high loads to which the corner pieces and lock pins are exposed with harsh military and/or humanitarian use thus act particularly on the lock pins. By contrast, the corner pieces are looked after, which is advantageous since the lock pins can be replaced more easily than the corner pieces.

In a further refinement the frames have first edge profile elements and second edge profile elements, which differ from the first edge profile elements, wherein the first and second edge profile elements each have a hollow chamber and each have two L-edges, which point away from the storage volume and which each extend parallel to the edge profile element, and wherein the first edge profile elements additionally have a support beam protruding into the storage volume, which support beam forms a further L-edge parallel to the edge profile element.

It has been found that the use of two different edge profile elements in the case of the intended purpose of the frames provided here enables a very economical implementation, although the number of different parts is indeed increased due to the two different edge profile elements. The support beam protruding into the storage volume and the additional L-edge of the first edge profile elements enables a simple fastening of transverse struts and/or floor panels, which can receive a high weight of the units, accessory parts or operating media. The first edge profile elements are therefore suitable in particular as horizontal edge profile elements in the frames of the retaining structure. By contrast, it is advantageously possible to dispense with the support beam for the second edge profile elements arranged vertically in this case, so as to save material and weight with maximum stability and so as to make the storage volume of the frames as large as possible.

In a further refinement the frames each have a closed floor panel and a closed ceiling panel opposite the floor panel. In the preferred exemplary embodiments the frames additionally have closed side walls, which can contain flaps and/or doors depending on the application. In some exemplary embodiments the floor panel, ceiling panel and side walls are formed using insulating material in order to protect in particular liquid operating supplies and/or temperature-sensitive accessory parts and units against extreme temperature changes.

Providing the frames with their own floor panels and ceiling panels protects the units, accessory parts and operating supplies arranged in the frames against damage during transport and use. In some advantageous exemplary embodiments working platforms can be provided on the ceiling panels, for example with the aid of insertable handrail parts. A raised working platform formed in this way is of great advantage especially in the case of decontamination of large-scale equipment, such as vehicles. The use of side walls at the individual frames also protects the housed units, accessory parts and operating supplies against environmental influences and damage during transport and use.

BRIEF DESCRIPTION OF THE DRAWINGS

It goes without saying that the above-mentioned features and the features yet to be explained hereinafter can be used not only in the specified combinations, but also in other combinations or in isolation, without departing from the scope of the present invention.

Exemplary embodiments are illustrated in the drawings and will be explained in greater detail in the following description. In the drawings:

FIG. 4 shows a corner piece of the frames from FIG. 3, FIG. 5 shows a lock pin for coupling two corner pieces from FIG. 4, FIG. 6 shows a first edge profile for the frames according to FIG. 3, FIG. 7 shows a second edge profile for the frames according to FIG. 3.

DESCRIPTION OF PREFERRED EMBODIMENTS

Figure 1:
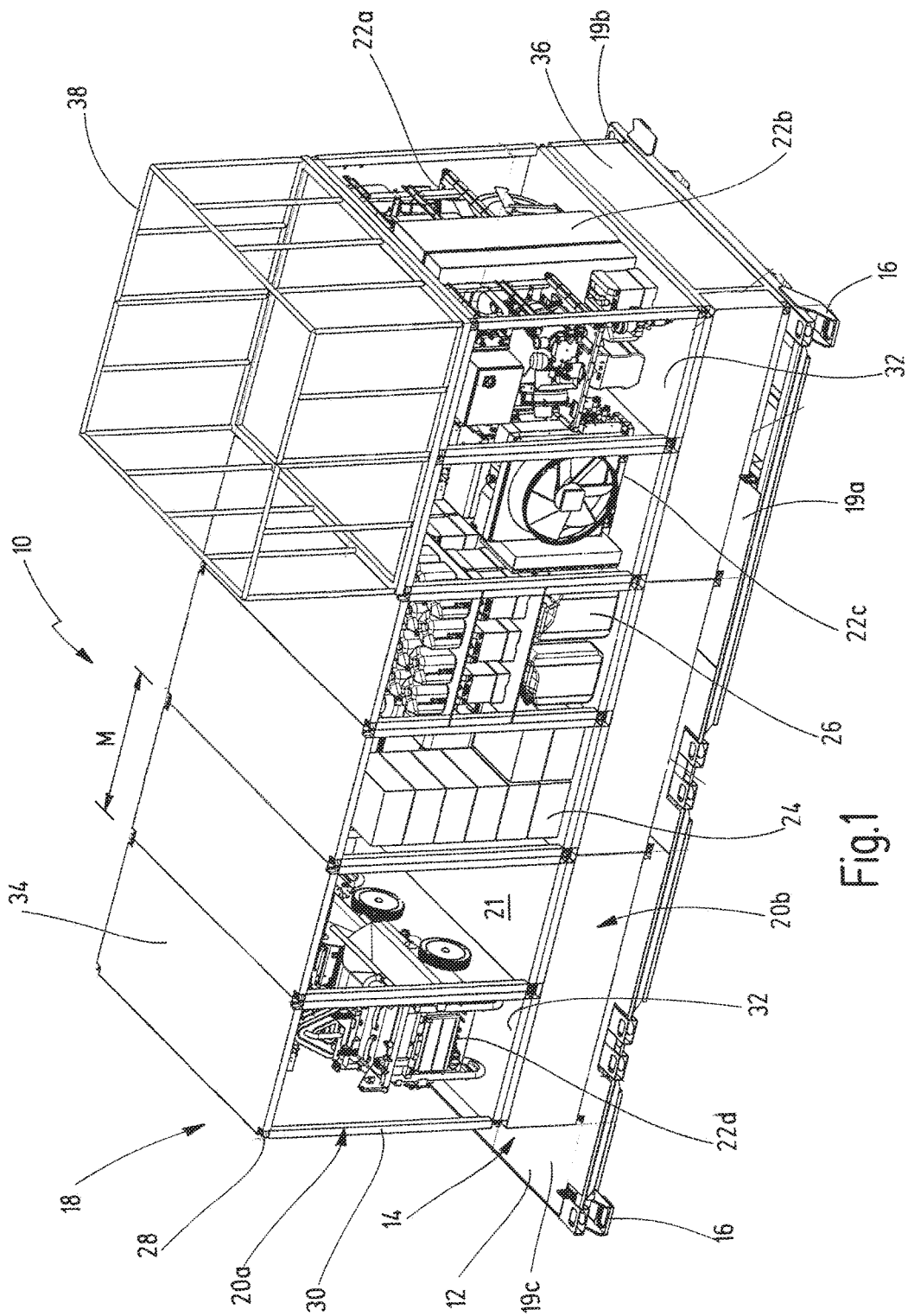
FIG. 1 shows an exemplary embodiment of the new system having two different types of frames and an optional working platform above some of the frames.

In FIG. 1 an exemplary embodiment of the new system is denoted in its entirety by the reference numeral 10. The device system 10 is here a decontamination system, which is designed for the radioactive decontamination, disinfection or detoxification of vehicles, devices, items of equipment and/or people (not illustrated here). A decontamination system of this type is a particularly preferred exemplary embodiment. However, the functional scope of the new device system can also concern or comprise other applications in principle. By way of example, the new device system may include a facility for purifying wastewater and for providing drinking water. In the preferred exemplary embodiments the device system is mobile in the sense that it can be brought in the form of a compact and self-contained unit to its place of use with the aid of suitable transport vehicles and/or helicopters.

The device system 10 has a base plate 12 having a defined placement surface 14 and having anchoring elements 16, which in the preferred exemplary embodiments enable detachable anchoring to a heavy goods vehicle (not illustrated here). In some exemplary embodiments the base plate is what is known as a flat rack, as is used for the transport of bulky goods in maritime transport, or the floor panel of what is known as an ISO container according to ISO standard 668. Flat racks and containers of this type have anchoring elements 16, which enable a detachable anchoring on the platform of a correspondingly formed heavy goods vehicle.

A retaining structure 18 is arranged on the placement surface 14 of the base plate 12 and is constructed in the manner described in greater detail hereinafter. In preferred exemplary embodiments the retaining structure 18 is arranged in the central region of the placement surface 14, such that a free edge region 19a, 19b remains on the base plate 12 on at least two opposite sides of the retaining structure 18. In the illustrated exemplary embodiment of FIG. 1 a free edge region 19c additionally remains transversely to the edge regions 19a, 19b. These edge regions are advantageous when the retaining structure is arranged in an ISO container of which the side walls can be opened, since said edge regions make it possible to access the retaining structure even when the side walls are closed.

The retaining structure 18 consists here of a total of nine frames 20. Here, the retaining structure 18 in this case includes six first frames 20a and three second frames 20b. The second frames 20b are arranged next to each other on the base plate 12 and are each fastened to the base plate 12 (which will be explained in greater detail further below). The first frames 20a are arranged on the second frames 20b and are fastened to the second frames 20b. As can be seen in the illustration of FIG. 1 the second frames 20b in this preferred exemplary embodiment each have twice the width of the first frames 20a and the same depth as the first frames 20a. Thus, a second frame 20b can receive exactly two first frames 20a. In other words the footprint of the second frames 20b is approximately twice as large here as the footprint of the first frames 20a. On the other hand the second frames 20b in this exemplary embodiment have only approximately a third of the height of the first frames 20a. The device system 10 is therefore provided with two different types of frames, which in each case are structurally identical, which is preferred for many exemplary embodiments. However, it is conceivable in principle to provide further frames having different dimensions in other exemplary embodiments.

The frames 20a, 20b each form a defined storage volume 21. The storage volumes 21 correspond to the interior surrounded by each frame 20.

As can be seen in the exemplary embodiment according to FIG. 1, the storage volumes 21 of the frames 20 are arranged above each other and next to each other, such that an overall volume formed from a plurality of separate storage volumes 21 and intended to receive objects which determine the functional scope of the device system 10 is provided in the central region of the placement surface 14.

In all preferred exemplary embodiments these objects include electrically operated units, such as pumps, electrical controllers, electrical heaters and further components, such as filters, hose lines, vacuum chambers, etc. In some exemplary embodiments the objects also include fuel-operated units, such as a diesel or multi-fuel burner for generating superheated steam and/or a generator for generating power. By way of example, a hot water high-pressure washer 22a inclusive of an electric control and operating unit and chemical tank 22b, and also a (diesel) generator 22c for power generation, and a high-pressure washer 22d are illustrated in FIG. 1, wherein the high-pressure washer 22d is housed in a frame 20a during the transport of the device system 10 and can be removed from the frame 20a for use in the field.

Here, large liquid tanks (not visible) are housed in the second frames 20b. The liquid tanks are used on the one hand to transport fresh water, which is required for the decontamination of people or objects, and they can also receive wastewater.

Furthermore, a plurality of accessory parts 24 and various operating supplies 26 are housed in the frames 20a. The operating supplies 26 include, for example, cleaning agents and decontaminants, fuels for the diesel or multi-fuel burner, or lubricants. The accessory parts 24 can include various small parts which are necessary for the use of the device system, such as spray lances or replacement parts for the units. The device system 10 may also include tents, shower trays or protective overalls for the operators (not illustrated here).

Together, the units, accessory parts and operating supplies determine the functional scope of the device system 10. This functional scope is generally predefined by the user purchasing a device system of this type, and the manufacturer of the device system has to provide the units, accessory parts and operating supplies required for the predefined functional scope in a form suitable for use and transport. The new retaining structure 18 of the device system 10 helps in this respect.

The structurally identical frames 20 here each have eight corner pieces 28 and twelve edge profile elements 30. The eight corner pieces 28 and twelve edge profile elements 30 together form a frame 20, which is stable enough to support the units, accessory parts and operating supplies housed therein. In the preferred exemplary embodiments at least some units 22a, 22b, 22c are arranged and fastened in a stationary manner in the frames. This means that the specified units remain in the frames 20 at the place of use and are used from there. When producing the device system 10 the corresponding units can therefore be assembled initially in the frames and then joined together. The frames 20 here form a universal retaining structure, which on account of its modular dimension M, which is uniform in this instance, facilitates an assembly of the device system 10 "in accordance with the building block principle".

Figure 8:
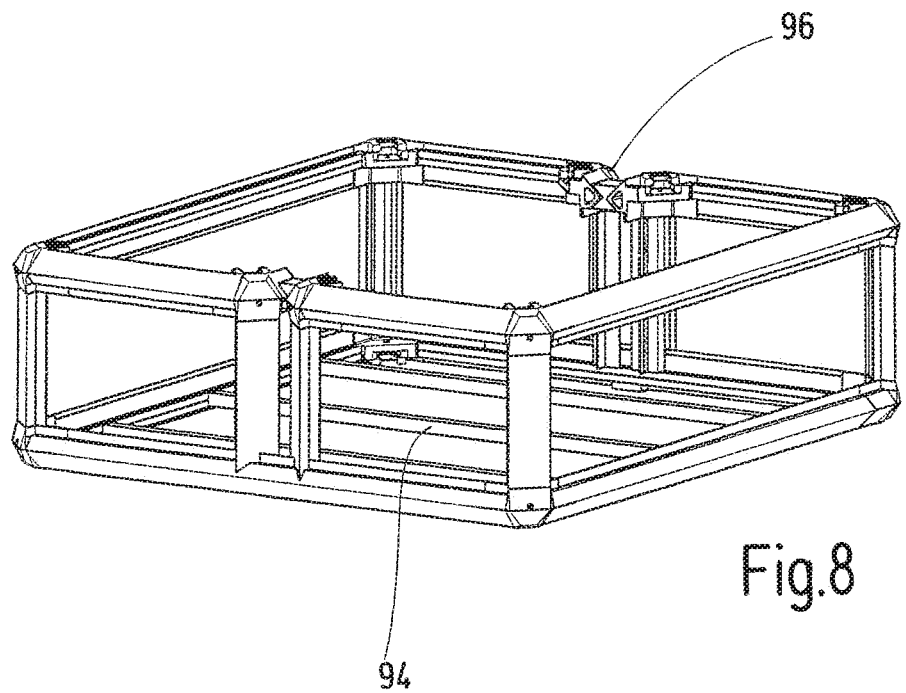
FIG. 8 shows a further frame of twice the width and short height.
Figure 9:
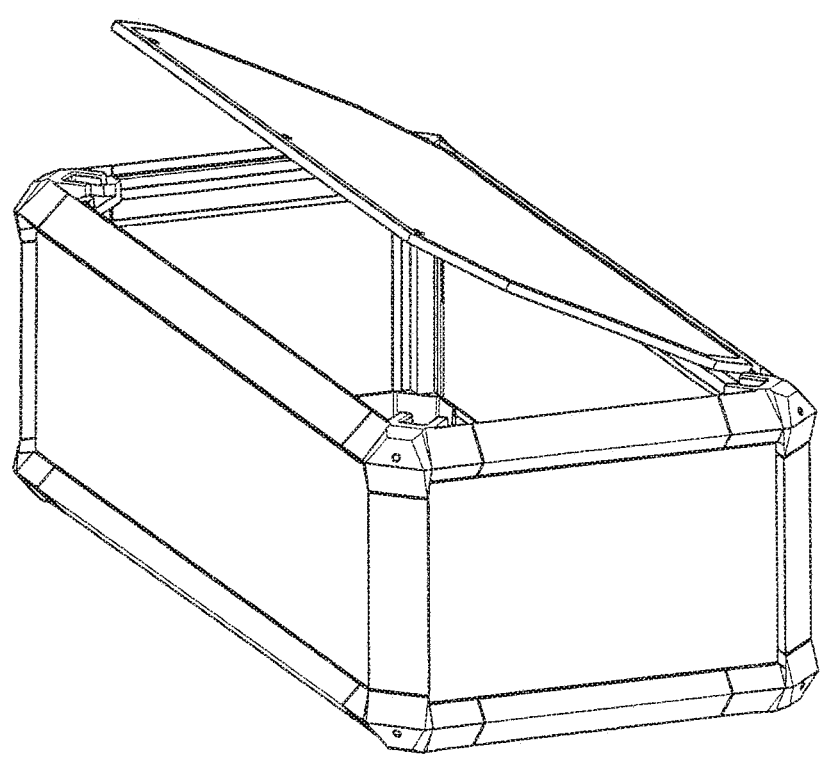
FIG. 9 shows a further frame of single width and short height and having floor and side walls and a hinged ceiling panel.

In some preferred exemplary embodiments each frame 20 has a stable floor panel 32, on which the units, accessory parts and/or operating supplies are held, and a ceiling panel 34 opposite the floor panel 32. Furthermore, individual frames or all frames can have their own side walls 36 (see FIG. 9). In the preferred exemplary embodiments the corner pieces 28 and edge profile elements 30 are formed such that the floor panel, ceiling panel and side walls 36 can be directly fastened to the edge profile elements 30. In some exemplary embodiments separate reinforcements struts (see FIG. 8, reference numeral 94) are welded in and/or screwed in in the region of the floor panel 32 in order to increase the load-bearing capacity of the floor panel 32. In some cases units are directly fastened to the supporting transverse struts. A floor panel 32 can in these cases be provided additionally in particular for thermal insulation.

Figure 2:
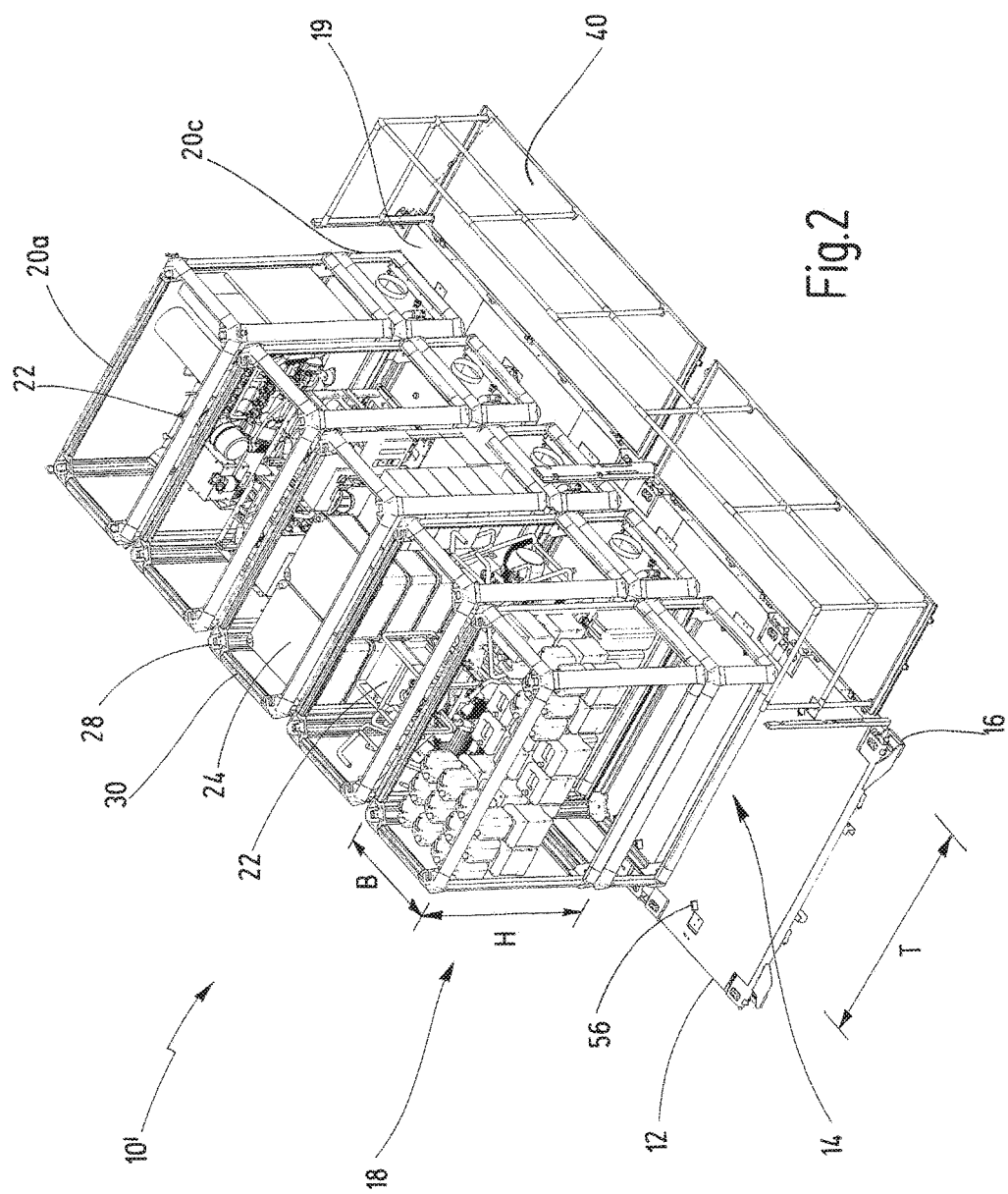
FIG. 2 shows a simplified illustration of an exemplary embodiment having a functional scope different from the exemplary embodiment in FIG. 1.

In some exemplary embodiments the device system has a working platform at the edge of the base plate 12, from which users can operate the device system (see FIG. 2). Alternatively or additionally the device system 10 can have a raised working platform, which for example facilitates the decontamination of tanks or other large-scale equipment. In the present exemplary embodiment a raised working platform of this type is provided with the aid of a handrail 38. The handrail 38 is, in the preferred exemplary embodiments, an accessory part which is housed in one or more of the frames 20a or 20b during transport of the device system 10 and which is fastened to the corner pieces 28 and/or edge profile elements 30 of the selected frames 20a at the place of use.

FIG. 2 shows a further exemplary embodiment of the device system 10, here denoted as the device system 10'. For improved clarity, floor panels, ceiling panels and side walls have been omitted in the illustration in FIG. 2. For the rest, the same reference signs denote the same elements as before.

The device system 10' has a retaining structure 18, which is formed by five first frames 20a and five further frames 20c. The frames 20a, 20c have a uniform modular dimension, wherein in this case all frames 20a, 20c have the same width B and the same depth T. All frames 20a, 20c in this exemplary embodiment therefore have the same footprint as that provided from the product of the width B and the depth T. The first frames 20a have a height H, which here is approximately three times the corresponding height of the further frames 20c. In this exemplary embodiment too, liquid tanks are advantageously arranged in the frames 20c. Units, accessory parts and operating supplies are arranged in the frames 20a and are fastened in a stationary manner where advantageous. The frames 20a, 20c each have identical corner pieces 28 and edge profile elements 30, which will be explained in greater detail hereinafter.

In accordance with an advantageous exemplary embodiment the device system 10' has a working platform 40, which can be fastened to the base plate 12 at the height of the base plate 12 and parallel to the placement surface 14. Together with the edge region 19, the working platform 40 forms an area on which an operator can comfortably stand in order to approach the units, accessory parts and/or operating media. The working platform 40 is particularly advantageous when the device system 10' is fastened on a heavy goods vehicle and is used from there.

In preferred exemplary embodiments the width B of the first frames 20a is approximately 90 cm (approximately 3 foot). The clear inner width is preferably 80 cm. The depth is approximately 200 cm (approximately 7 foot). The height of the first frames 20a is, in advantageous exemplary embodiments, approximately 150 cm (5 foot). These dimensions have proven to be very advantageous in order to construct, with the frames 20a, 20b, 20c, device systems that can be conveyed using established and tried and tested transport means, in particular using heavy goods vehicles and helicopters. In preferred exemplary embodiments the retaining structure 18 consists exclusively of frames 20a, 20b (see FIG. 1) and/or 20c, i.e. the number of frames used is limited to two or at most three structurally identical types.

Figure 3:
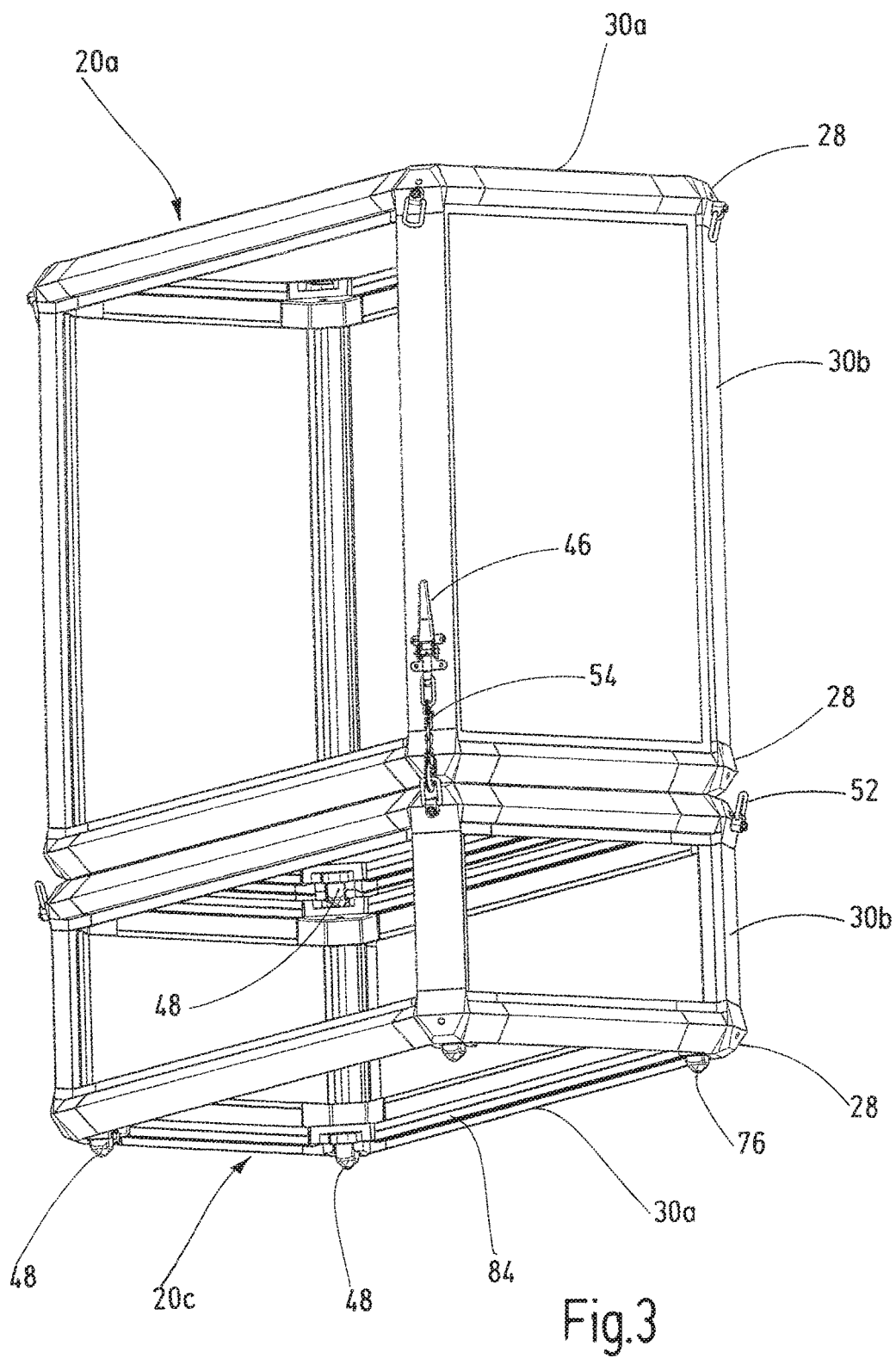
FIG. 3 shows a first and a second frame, which are used together in the exemplary embodiment according to FIG. 2.

FIG. 3 shows an enlarged illustration of a first frame 20a and a further frame 20c from the device system 10' of FIG. 2. As can be seen, the first frame 20a and the further frame 20c here are detachably fastened to one another with the aid of a clamping mechanism 46 and with the aid of lock pins 48. The lock pins 48 (see FIG. 5) are inserted into a pocket-like indentation 50 (see FIG. 4), which is formed on each of the corner pieces 28. The lock pins 48, in combination with the corner pieces 28, ensure that the frames 20a, 20c are fastened in a very robust and stable manner in two of the three possible spatial directions, wherein these two spatial directions lie horizontally in the preferred exemplary embodiments. The clamping mechanism 46, which is illustrated here only at one location, is used to fix the frames 20a, 20c in the third spatial direction. In the preferred exemplary embodiments corresponding clamping mechanisms 46 are arranged on all four corner pieces 28, at which two frames arranged on top of each other rest against one another. Accordingly, in the preferred exemplary embodiments, two frames 20a, 20c are in each case fastened to one another via four corner piece pairs resting against one another, a lock pin 48 inserted into each corner piece pair, and four clamping mechanisms 46.

As is illustrated in FIG. 3 by way of example, all of the upper corner pieces 28 have an eyelet 52, in which a chain 54 can be latched. The chain 54 can be tensioned with the aid of the clamping mechanism 46, which here includes an eccentric by way of example, in order to thus fix, in the vertical direction, the frames 20a, 20c arranged on top of each other. In other exemplary embodiments the clamping mechanism 46 includes a turnbuckle having two oppositely directed screw threads (right-hand thread and left-hand thread) arranged axially relative to one another. The lock pins 48 in the corner pieces 28 ensure stable fastening in the horizontal direction.

In the preferred exemplary embodiments the frames 20 are fastened on the base plate 12 in a similar manner. For this purpose, further indentations 56 (FIG. 2) are arranged in the base plate 12. The free ends of the lock pins in the corner pieces 28 of each of the frames 20b or 20c arranged at the bottom protrude into the holes or indentations in the base plate 12 in order to ensure a fixing in the horizontal direction. In the vertical direction the frames are then clamped on the base plate 12 using a clamping mechanism 46 and a chain 54.

As can be seen in FIG. 4 each corner piece here has three pins 58a, 58b, 58c arranged orthogonally to one another. In the preferred exemplary embodiments the pins 58 have a polygonal cross section, which in particular has a largely triangular basic shape. The pins 58 are interconnected in a materially bonded manner via a middle part 60. The middle part 60 has a pocket-like indentation 50 on a side facing away from one of the pins (here the pin 58c), said indentation being delimited by a U-shaped profile element 62. The U-shaped profile element 62 has a planar outer face 64, which forms a defined elevation on the associated corner piece. In other words, the planar outer face 64 forms a defined footprint area, at which two opposite corner pieces 28 can rest against one another in a planar manner without the edge profiles 30 of the associated frames contacting one another. The U-shaped profile element 62 forms an undercut in the indentation 50, the head 68 of a lock pin 48 being held in said undercut. The middle part advantageously has a bore 70, and a threaded bore 72 is arranged in the head of the lock pin 48 and is aligned with the bore 70 when the lock pin 48 is inserted. The lock pin 48 can be secured by the bore 70 by screwing a screw (not illustrated here) through the bore 70 into the bore 72. The free end 74 of the lock pin 48 in some exemplary embodiments has a further bore 76, into which a screw likewise can be screwed (not illustrated here) through the indentation 50 of the corner piece arranged below.

In preferred exemplary embodiments the corner pieces 28 are cast pieces made of aluminum or an aluminum alloy having a hardness that is harder than the material from which the lock pins 48 are produced. In this case the lock pins 48 act as wearing parts, which can be replaced as necessary following frequent detachment and clamping of frames, without having to disassemble the frames themselves.

FIGS. 6 and 7 illustrate advantageous edge profile elements, which are fitted onto the pins 58 of the corner pieces 28 in the preferred exemplary embodiments. FIG. 6 shows an edge profile element 30a, which in the preferred exemplary embodiments is used for the horizontally arranged edge profile elements. FIG. 7 shows a further edge profile element 30b, which in the preferred exemplary embodiments is used for the vertical edge profile elements. As can be seen, the edge profile elements 30a, 30b are different.

Each of the edge profile elements 30a, 30b has a hollow chamber 80. In the case of the edge profile element 30b the hollow chamber 80b has a triangular cross section, such that the edge profile 30b can be placed with an accurate fit onto the pin 58c, which is triangular in cross section. The hollow chamber 80a of the edge profile element 30a has a largely triangular cross section, but has a straight edge 82 instead of a third point. The hollow chamber 80a here therefore has a polygonal cross section having four corners, wherein the basic shape is approximated with that of a triangle. This form has proven to be advantageous because it enables high stability alongside relatively low weight.

The edge profile 30a also has an integrated support beam 84, which in the case of the frames 20 points toward the storage volume 21 (see FIG. 3). The support beam 84 enables simple fastening of reinforcement struts (not illustrated here), which is advantageous in particular in the region of the floor panel 32 and the ceiling panel 34.

In addition, each edge profile element 30a forms three L-shaped edges 86a, 86b, 86c. The L-edges 86a, 86b point with their "opening" away from the storage volume 21 and each form a contact and mounting surface for the floor panel 32, ceiling panel 34 and/or side walls 36. The third L-edge 86c points toward the storage volume 21. Here, a floor panel can be mounted advantageously above support struts (not illustrated here) and is then additionally stabilized by the support struts.

The vertical edge profiles 30b differ from the horizontal edge profiles 30a above all in that the support beam 84 is omitted. Instead, the edge profiles 30b here have two wings 88a, 88b, which on the whole form four L-edges 90a to 90d. In principle, it would be sufficient for the vertical edge profiles 30b to form just two L-edges 90a, 90d, which again serve as mounting surfaces for fastening of the side walls. The two advantageous L-edges 90a, 90d can be provided with low material weight by means of the wings 88. In addition superstructures, for example units and/or accessory parts, can be fastened in the interior of the frames in the inner edges 90b and 90c. In order to facilitate the mounting of transverse struts, superstructures and/or ceiling, floor and/or side panels, the support beam 84 and the wings 88 each have marked lines 98, which in the preferred exemplary embodiments are formed as continuous linear indentations.

In all preferred exemplary embodiment the edge profile elements 30a, 30b are aluminum strand cast profile elements. The floor panels, ceiling panels and side walls are sandwich panels having a plastic core, which is covered by two aluminum or glass-fiber laminations. The sandwich panels are advantageously screwed and/or glued into the L-edges 86, 90 of the edge profile elements 30.

As can be seen in FIG. 4 the corner pieces 28 in the region of the pins 58 are formed with numerous surfaces inclined relative to one another, which promotes the removal of the corner pieces 28 from the casting molds (not illustrated here). On the other hand, the inclined outer faces of the corner pieces 28 make it difficult to laterally connect two corner pieces 28 other than at the U-shaped profile elements 62. In some exemplary embodiments wedge pieces (see FIG. 8, reference numeral 96) can therefore be welded in between two adjacent corner pieces in order to provide a "double corner" with six pins in this cost-effective manner. With the double corner it is possible to provide stable frames having twice or three times the width of the modular dimension very economically. In the preferred exemplary embodiments, however, the frames arranged next to each other are not fastened to each other, but are arranged with a lateral spacing of approximately 20 to 30 mm. in some exemplary embodiments rubber buffers can be placed between frames arranged next to each other in order to absorb noise caused by impacts or contact.

One advantage of the preferred frames having the corner pieces 28 lies in the fact that the corner pieces 28 are coupled to one another merely via the lock pins and the clamping mechanism. The preferred frames therefore forego movable parts for mutual coupling.

What is claimed is:

1. A mobile decontamination system for at least one of radioactive decontamination, disinfection or detoxification, the mobile decontamination system comprising:
    a plurality of power-operated units including at least one pump for recirculating, conveying or discharging liquids, a heater, and a process controller for controlling the at least one pump and the heater,
    a water tank,
    cleaning agents or decontaminants,
    a load-bearing base plate having a defined placement surface, and
    a retaining structure fastened on the defined placement surface and designed to hold the plurality of power-operated units, the water tank, and the cleaning agents or decontaminants on the load-bearing base plate during transport of the mobile decontamination system,
    wherein the retaining structure is formed from a plurality of self-supporting, structurally identical, cuboid-shaped frames which are arranged next to each other or on top of each other and which are fastened to the load-bearing base plate,
    wherein each frame of the plurality of self-supporting, structurally identical, cuboid-shaped frames, comprises:
        eight corner pieces disposed at corners of each frame; and
        twelve frame edge profile elements disposed along edges that extend between the corners of each frame, wherein each frame edge profile element includes a cross-section of material that spans between and contacts an adjacent and opposing pair of corner pieces, and wherein the eight corner pieces and the twelve frame edge profile elements together enclose a defined cuboid-shaped storage volume for each frame,
    wherein the plurality of power-operated units are fixedly installed in respective ones of the defined storage volume per frame, and wherein the plurality of power-operated units are operable while fixedly installed.

2. The mobile decontamination system of claim 1, wherein the plurality of self-supporting, structurally identical, cuboid-shaped frames occupy a central region of the defined placement surface, such that a free edge region remains on the load-bearing base plate on at least two sides.

3. The mobile decontamination system of claim 2, further comprising at least one mobile working platform designed to be positioned at the height of the load-bearing base plate at the free edge region.

4. The mobile decontamination system of claim 1, wherein the plurality of power-operated units further comprise a fuel-operated generator or a fuel-operated burner.

5. The mobile decontamination system of claim 1, wherein the plurality of self-supporting, structurally identical, cuboid-shaped frames have a uniform modular dimension in terms of width, depth or height.

6. The mobile decontamination system of claim 1, wherein the plurality of self-supporting, structurally identical, cuboid-shaped frames includes first frames and second frames, the first frames comprising a first footprint having a first width and a first depth and comprising a first height, the second frames comprising a second footprint having a second width and a second depth and comprising a second height, wherein the second depth is the same as the first depth, and wherein the second height is approximately a third of the first height.

7. The mobile decontamination system of claim 6, wherein the second width is twice the first width.

8. The mobile decontamination system of claim 6, wherein the first width is approximately 90 cm and the first depth is approximately 200 cm.

9. The mobile decontamination system of claim 1, wherein the eight corner pieces each have three pins arranged orthogonally to one another, and wherein each pin of the three pins is permanently connected to at least one frame edge profile element of the twelve frame edge profile elements.

10. The mobile decontamination system of claim 1, wherein the eight corner pieces each have a pocket-like indentation, which is delimited on one side by a U-shaped profile element, which forms an undercut in the pocket-like indentation.

11. The mobile decontamination system of claim 10, wherein the U-shaped profile element has a planar outer face, which forms a defined elevation on each associated corner piece.

12. The mobile decontamination system of claim 1, further comprising a plurality of T-shaped lock pins mechanically connecting adjacently arranged corner pieces of a first frame of the plurality of self-supporting, structurally identical, cuboid-shaped frames to adjacently arranged corner pieces of a second frame of the plurality of self-supporting, structurally identical, cuboid-shaped frames, wherein the first frame is arranged on top of the second frame.

13. The mobile decontamination system of claim 12, wherein the eight corner pieces are produced from a first material, and the plurality of T-shaped lock pins are produced from a second material, which is softer than the first material.

14. The mobile decontamination system of claim 1, wherein the plurality of self-supporting, structurally identical, cuboid-shaped frames each have first frame edge profile elements and second frame edge profile elements, which differ from the first frame edge profile elements, wherein the first and second frame edge profile elements each have a hollow chamber and each have two L-edges, which point away from the defined storage volume and which each extend parallel to a length of the first and second frame edge profile elements, respectively, and wherein the first frame edge profile elements additionally have a support beam protruding into the defined storage volume, which support beam forms a further L-edge parallel to the length of the first frame edge profile elements.

* * * * *